United States Patent
Lin (10) Patent No.: US 10,726,114 B2
(45) Date of Patent: Jul. 28, 2020

(54) BIOLOGICAL FEATURE DATA DETECTION METHOD, BIOLOGICAL FEATURE IDENTIFICATION APPARATUS AND ELECTRONIC TERMINAL

(71) Applicant: SHENZHEN GOODIX TECHNOLOGY CO., LTD., Shenzhen (CN)

(72) Inventor: Jinhui Lin, Shenzhen (CN)

(73) Assignee: SHENZHEN GOODIX TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 15/708,086

(22) Filed: Sep. 18, 2017

(65) Prior Publication Data

US 2018/0307817 A1    Oct. 25, 2018

Related U.S. Application Data

(63) Continuation of application No. PCT/CN2017/081384, filed on Apr. 21, 2017.

(51) Int. Cl.
*G06K 9/00* (2006.01)
*G06F 21/32* (2013.01)
(Continued)

(52) U.S. Cl.
CPC ......... *G06F 21/32* (2013.01); *G06K 9/00033* (2013.01); *G06K 9/00885* (2013.01);
(Continued)

(58) Field of Classification Search
None
See application file for complete search history.

(56) References Cited

U.S. PATENT DOCUMENTS

| 8,744,140 B2 * | 6/2014 | Baughman | G06F 21/32 351/205 |
| 8,750,575 B2 * | 6/2014 | Baughman | G06F 21/32 351/205 |

(Continued)

FOREIGN PATENT DOCUMENTS

| CN | 105550672 A | 5/2016 |
| CN | 105893988 A | 8/2016 |

(Continued)

OTHER PUBLICATIONS

Shin et al., "New iris recognition method for noisy iris images", Pattern Recognition Letters 33 (2012) 991-999 (Year: 2012).*

*Primary Examiner* — Soo Jin Park (57) ABSTRACT

Embodiments of the present disclosure provide a biological feature data detection method, a biological feature identification apparatus and an electronic terminal. The method includes: determining, based on a first illumination environment parameter in an ambient environment at a biological feature registration stage and a second illumination environment parameter in an ambient environment at a biological feature matching stage, an ambient illumination environment variation factor at the biological feature matching stage relative to the biological feature registration stage; and adjusting a quality influence factor of biological feature data at the biological feature matching stage according to the ambient illumination environment variation factor at the biological feature matching stage relative to the biological feature registration stage, and detecting the biological feature data at the biological feature matching stage.

5 Claims, 5 Drawing Sheets

Based on a first ambient illumination environment light intensity in an ambient environment at a biological feature registration stage and a second ambient illumination environment light intensity in an ambient environment at a biological feature matching stage, determine an ambient illumination environment variation factor at the biological feature matching stage relative to the biological feature registration stage — S201

Adjust a second exposure time of the sensing unit at the biological feature matching stage according to the ambient illumination environment variation factor at the biological feature matching stage relative to the biological feature registration stage and a first exposure time of the sensing unit at the biological feature registration stage — S202

Control the sensing unit according to the second exposure time of the sensing unit at the biological feature matching stage to sense light, to detect the biological feature data at the biological feature matching stage — S203

(51) Int. Cl.
*G06K 9/20* (2006.01)
*G06K 9/03* (2006.01)
*H04N 1/32* (2006.01)
*G06F 21/60* (2013.01)

(52) U.S. Cl.
CPC .......... *G06K 9/036* (2013.01); *G06K 9/2027*
(2013.01); *H04N 1/32* (2013.01); *A61B*
*2560/0462* (2013.01); *G06F 21/60* (2013.01)

(56) References Cited

U.S. PATENT DOCUMENTS

2003/0016297 A1* 1/2003 Shigeta .............. G06K 9/00013
348/304
2011/0033090 A1* 2/2011 Baughman .............. G06F 21/32
382/117
2018/0012007 A1* 1/2018 Kim ........................ G06F 21/32

FOREIGN PATENT DOCUMENTS

| CN | 106250825 | A | 12/2016 |
| CN | 106295596 | A | 1/2017 |
| CN | 106469301 | A | 3/2017 |
| CN | 107223256 | A | 9/2017 |
| JP | 2005165943 | A | 6/2005 |
| WO | 2016/117755 | A1 | 7/2016 |
| WO | 2016/176989 | A1 | 11/2016 |

* cited by examiner

BIOLOGICAL FEATURE DATA DETECTION METHOD, BIOLOGICAL FEATURE IDENTIFICATION APPARATUS AND ELECTRONIC TERMINAL

CROSS-REFERENCE TO RELATED APPLICATIONS

The present application is a continuation of international application No. PCT/CN2017/081384, filed on Apr. 21, 2017, which is hereby incorporated by reference in its entirety.

TECHNICAL FIELD

Embodiments of the present disclosure relate to the field of information security, and in particular, relate to a biological feature data detection method, a biological feature identification apparatus, and an electronic terminal.

BACKGROUND

With application of the fingerprint feature identification technology in mobile terminals, fingerprint-based authentication has replaced the traditional password-based authentication, gesture-based authentication and the like. In this way, the authentication may be conveniently implemented as long as a finger of a user is in contact with a sensor, without requiring other operations. This greatly improves use convenience of the mobile terminal while ensuring mobile terminal security, and accordingly, the fingerprint feature identification function becomes a standard configuration of the mobile terminals or even the traditional electronic products.

In the related art, with respect to the mobile terminal products or even the traditional electronic products, the fingerprint feature identification technology is typically integrated at a Home key at the front side of the product, or is arranged as a dedicated fingerprint feature identification key on the rear side of the product. During use, the fingerprint feature identification function is implemented by pressing the Home key at the front side or the fingerprint feature identification key on the rear side.

Implementation of the fingerprint feature identification function typically includes two stages: a fingerprint feature registration stage and a fingerprint feature matching stage. At the fingerprint feature registration stage, fingerprint feature data is pre-acquired. At the fingerprint feature matching stage, fingerprint feature data is acquired in real time, and is compared with the pre-acquired fingerprint feature data, thereby completing validity authentication.

However, at the fingerprint feature registration stage and the fingerprint feature matching stage, the fingerprint feature data is acquired at generally different environments. Taking the fingerprint feature identification being implemented based on light reflection as an example, ambient illumination environments at the fingerprint feature registration stage and the fingerprint feature matching stage are different, and thus the photosensitive environments at the fingerprint feature matching stage are different. As such, the fingerprint feature identification effect at the fingerprint feature matching stage is poor.

SUMMARY

Embodiments of the present disclosure are intended to provide a biological feature data detection method, a biological feature identification apparatus and an electronic terminal, to at least solve the above problem in the related art.

To achieve the objectives of embodiments of the present disclosure, embodiments of the present disclosure provide a biological feature data detection method. The method includes:

determining, based on a first illumination environment parameter in an ambient environment at a biological feature registration stage and a second illumination environment parameter in an ambient environment at a biological feature matching stage, an ambient illumination environment variation factor at the biological feature matching stage relative to the biological feature registration stage; and adjusting a quality influence factor of biological feature data at the biological feature matching stage according to the ambient illumination environment variation factor at the biological feature matching stage relative to the biological feature registration stage, and detecting the biological feature data at the biological feature matching stage.

Embodiments of the present disclosure further provide a biological feature identification apparatus. The apparatus includes: a biological feature detection apparatus and a biological feature detection driving unit. The biological feature detection driving unit is configured to: determine, based on a first illumination environment parameter in an ambient environment at a biological feature registration stage and a second illumination environment parameter in an ambient environment at a biological feature matching stage, an ambient illumination environment variation factor of the biological feature detection apparatus at the biological feature matching stage relative to the biological feature registration stage; and adjust a quality influence factor of biological feature data at the biological feature matching stage according to the ambient illumination environment variation factor at the biological feature matching stage relative to the biological feature registration stage, and drive the biological feature detection apparatus to detect the biological feature data at the biological feature matching stage.

Embodiments of the present disclosure further provide an electronic terminal. The terminal includes: a light sensor and the biological feature identification apparatus as described above. The light sensor is configured to determine a first illumination environment parameter in an ambient environment at a biological feature registration stage and a second illumination environment parameter in an ambient environment at a biological feature matching stage respectively.

According to embodiments of the present disclosure, based on a first illumination environment parameter in an ambient environment at a biological feature registration stage and a second illumination environment parameter in an ambient environment at a biological feature matching stage, an ambient illumination environment variation factor of the biological feature detection apparatus at the biological feature matching stage relative to the biological feature registration stage is determined; and a quality influence factor of biological feature data at the biological feature matching stage is adjusted according to the ambient illumination environment variation factor at the biological feature matching stage relative to the biological feature registration stage, and the biological feature detection apparatus is driven to detect the biological feature data at the biological feature matching stage. In this way, the problem that the fingerprint feature identification effect is poor due to different environments where the biological feature data is formed at the biological feature identification stage and the biological feature registration stage, and the biological feature identification performance is improved.

DETAILED DESCRIPTION

Practice of the present application is described in detail with reference to drawings and specific embodiments, such that the practice of addressing the technical problem using the technical means according to the present application and achieving the technical effects may be better understood and conducted.

According to embodiments of the present disclosure hereinafter, based on a first illumination environment parameter in an ambient environment at a biological feature registration stage and a second illumination environment parameter in an ambient environment at a biological feature matching stage, an ambient illumination environment variation factor at the biological feature matching stage relative to the biological feature registration stage is determined; and a quality influence factor of biological feature data at the biological feature matching stage is adjusted according to the ambient illumination environment variation factor at the biological feature matching stage relative to the biological feature registration stage; the biological feature detection apparatus is driven to detect the biological feature data at the biological feature matching stage. In this way, the problem that the fingerprint feature identification effect is poor due to different environments where the biological feature data is formed at the biological feature identification stage and the biological feature registration stage, and the biological feature identification performance is improved.

The biological feature data detection method according to the embodiment of the present disclosure may be applied to an electronic terminal having a biological feature detection function, for example, a mobile terminal such as a smart phone, a tablet computer, or the like. The biological feature may include, but not limited to, a fingerprint, a heart rate, blood oxygen concentration and the like. The electronic terminal may detect the biological feature using a biological feature identification apparatus. Taking fingerprints as an example, the electronic terminal may include a fingerprint feature identification apparatus.

Figure 9:
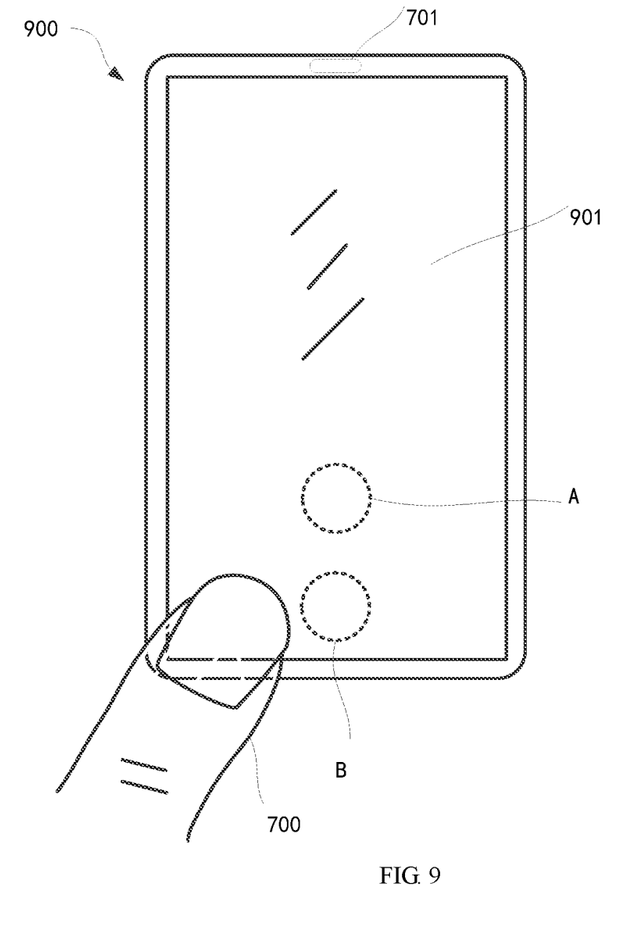
FIG. 9 is a specific schematic diagram illustrating a specific application of the biological feature detection apparatus in the electronic terminal according to an embodiment of the present disclosure.

Referring to FIG. 9, a specific schematic diagram illustrating a specific application of the biological feature detection apparatus in an electronic terminal according to an embodiment of the present disclosure is provided. In this embodiment, the biological feature identification apparatus is described by taking a fingerprint feature identification apparatus as an example.

As an implementation, referring to FIG. 9, the effective fingerprint detection ranges A and B of the fingerprint feature identification apparatus may cover at least a portion of the display region of a display screen 901 of the electronic terminal 900. Fingerprint feature detection may be performed by the fingerprint feature identification apparatus for a user when the user presses a corresponding region A or B of the display screen 901 using a finger 700, such that fingerprint detection function is implemented in the display region. For example, the display screen may be an OLED display screen, the fingerprint feature identification apparatus may be an optical fingerprint identification apparatus, which may be practiced by being arranged under the display screen (Under display) or being integrated in the display screen (In display). For example, the fingerprint feature identification apparatus may be an independent function part which is directly arranged under the display region of the display screen, and some functions of the display screen can be used by the fingerprint feature identification apparatus, for example, some OLED pixel units of the OLED display screen may be used as a light source (that is, an OLED light source) for the fingerprint feature identification apparatus.

In addition, as illustrated in FIG. 9, the electronic terminal 900 includes a light sensor 701. The light sensor 701 may be arranged on a periphery of the display region of the display screen 901, for example, arranged at a top edge of the electronic terminal 900 and configured to detect an ambient environment light intensity. Alternatively, the light sensor 701 may be integrated in the display region of the display screen 901. For example, when the electronic terminal 900 implements the above-described fingerprint detection function in the display region by using an optical fingerprint identification apparatus, the light sensor 701 may be integrated in the fingerprint feature identification apparatus. For example, the light intensity may be detected by using a portion of fingerprint sensing units in the fingerprint feature identification apparatus, or by using a light sensing unit arranged on a periphery of a fingerprint sensing unit array.

It should be understood that although the above examples are described by taking the biological feature identification apparatus being the fingerprint feature identification apparatus as an example, in practice, when being applied in other biological feature detections, the biological feature identification apparatus may also employ a similar structure to implement the corresponding biological feature detection in the display region. In addition, the number and specific position of effective fingerprint detection ranges may be customized according to user preferences.

Figure 1:
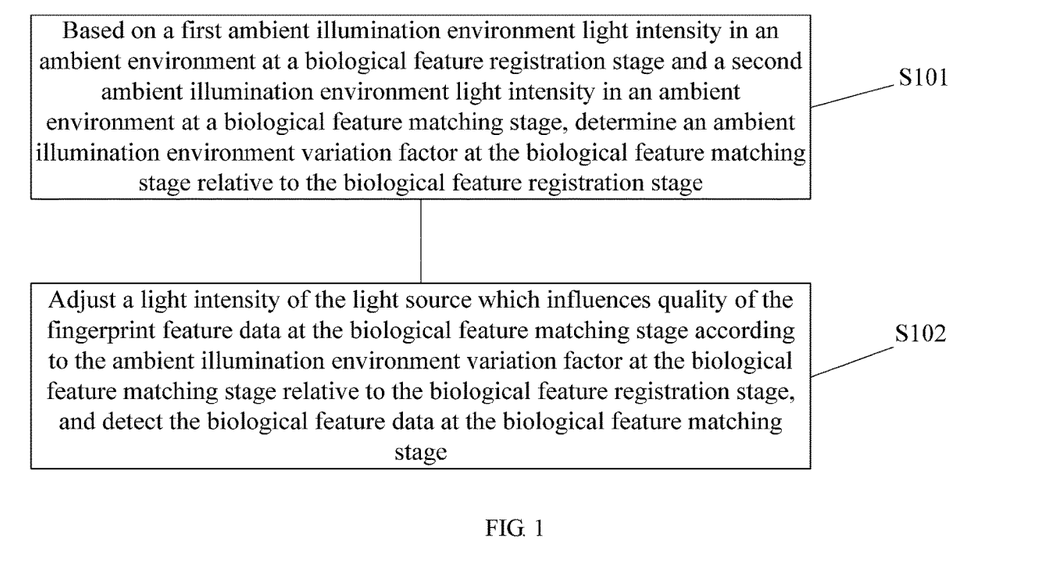
FIG. 1 is a schematic flowchart of a biological feature data detection method according to a first embodiment of the present disclosure.

FIG. 1 is a schematic flowchart of a biological feature data detection method according to a first embodiment of the present disclosure. In this embodiment, quality of biological feature data may be understood as whether the biological feature data is good or poor. For example, if the biological feature data is image-based data, the quality may refer to clarity, noise or the like of images. A quality influence factor of the biological feature data may refer to any factor influencing whether the biological feature data is good or poor. For example, if the biological feature data is the image-based data, the quality influence factor may be an illumination environment in which the images are formed, an operation parameter for acquiring the images or the like. As illustrated in FIG. 1, the method according to this embodiment includes the following steps:

S101: based on a first ambient illumination environment light intensity in an ambient environment at a biological feature registration stage and a second ambient illumination environment light intensity in an ambient environment at a biological feature matching stage, an ambient illumination environment variation factor at the biological feature matching stage relative to the biological feature registration stage is determined.

In this embodiment, fingerprint feature data is pre-acquired at the biological feature registration stage, and the fingerprint feature data is used for comparison with fingerprint feature data acquired at the biological feature matching stage, so as to perform validity authentication.

In this embodiment, the biological feature may be a fingerprint feature. Description is given using implementation of fingerprint feature identification based on optical reflection as an example, a fingerprint sensor for implementing the fingerprint feature identification may include a light source and a sensing unit. Light emitted by the light source is shaded by a finger or other objects, and then is reflected to and received by the sensing unit. Fingerprint feature data is generated according to the light received by the sensing unit. The fingerprint feature data is specifically a fingerprint feature image. It should be noted that, in this embodiment, the light source of the fingerprint sensor is independent of the light source of the display screen, and in other embodiment, the light source may share the light source of the display screen, for example, an organic light-emitting diode (OLED) in an OLED display screen. Details are not given in the accompanying drawings.

In this embodiment, a first ambient illumination environment light intensity (represented by n1) at the biological feature registration stage and a second ambient illumination environment light intensity (represented by n2) at the biological feature matching stage may be specifically determined by using a light sensor. The light sensor may be a light sensor that is originally configured on the electronic terminal, or may be a light sensor that is additionally configured to achieve the objective of this embodiment.

S102: A light intensity of the light source, which influences quality of the biological feature data at the biological feature matching stage, is adjusted according to the ambient illumination environment variation factor at the biological feature matching stage relative to the biological feature registration stage, and the biological feature data is detected at the biological feature matching stage.

Adjustment of the light intensity may enable quality of the biological feature data at the biological feature matching stage to be at least approximate to quality of the biological feature data at the biological feature registration stage.

In this embodiment, in step S102 for adjusting the light intensity of the light source of a biological feature detection apparatus at the biological feature matching stage, a second light intensity (represented by s2) of the light source at the biological feature matching stage may be adjusted according to the ambient illumination environment variation factor at the biological feature matching stage relative to the biological feature registration stage and a first light intensity (represented by s1) of the light source at the biological feature registration stage. In this embodiment, the quality of the biological feature data may specifically refer to the clarity of a fingerprint feature image. However, it should be noted that the quality of the biological feature data is not limited the clarity of the fingerprint feature image, which may alternatively refer to noise of the image or the like.

Specifically, as described above, the first light intensity s1 may be obtained by analyzing a driving signal applied to the light source at the biological feature registration stage. Similarly, after the second light intensity is obtained, the driving signal applied to the light source may be controlled to make the light source reach the second light intensity at the biological feature registration stage.

Herein description is given with reference to a specific example:

$$s2 = \alpha * s1 * \frac{n_1}{n_2} \quad (1)$$

In formula (1), n1 represents a first ambient illumination environment light intensity, n2 represents a second ambient illumination environment light intensity, s1 represents the first light intensity, s2 represents a second light intensity, n1/n2 represents an ambient illumination environment variation factor, and a represents a filter coefficient, which reflects a degree of performing light filtering for the interference light other than the light source.

In this embodiment, a light intensity variation is used as the ambient illumination environment variation factor. However, it should be noted that any indictor that reflects a variation degree of the ambient illumination environment at the biological feature registration stage and the biological feature matching stage may apply, and the ambient illumination environment variation factor is not limited to the light intensity.

As seen from formula (1), the second light intensity is inversely proportional to the second ambient illumination environment light intensity. The greater the second ambient illumination environment light intensity, the smaller the second light intensity; and on the contrary, the smaller the second ambient illumination environment light intensity, the greater the second light intensity. The second light intensity is proportional to the first light intensity. The greater the first light intensity, the greater the second light intensity; and on the contrary, the smaller the first light intensity, the smaller the second light intensity.

After the second light intensity s2 is determined according to formula (1), the driving signal of the light source is correspondingly adjusted, such that the light emitted by the light source reaches the second light intensity s2, and thus photosensitive environments at the fingerprint feature registration stage and the fingerprint feature matching stage are similar as much as possible or even the same. In this way, the fingerprint feature images at the biological feature registration stage and the biological feature matching stage are at least approximate or even the same in terms of clarity. For example, average values of the fingerprint feature images are similar or even the same, such that the fingerprint identification performance is ensured.

In addition to the above manner of adjusting the light intensity of the light source, an operation parameter of the sensing unit at the biological feature matching stage may be adjusted, according to the ambient illumination environment variation factor at the biological feature matching stage relative to the biological feature registration stage, and an operation parameter of the sensing unit at the biological feature registration stage, such that the photosensitive environments at the fingerprint feature registration stage and the fingerprint feature matching stage are similar as much as possible or even the same. The operation parameter may be an exposure time and/or an ADC gain coefficient of the sensing unit. A second embodiment and a third embodiment hereinafter are exemplarily described by adjusting the exposure time and the ADC gain coefficient of the sensing unit respectively.

Different from the above embodiment, in the second embodiment and the third embodiment hereinafter, the operation parameter of the sensing unit rather than the light intensity of the light source is adjusted, and therefore, at the biological feature matching stage and the biological feature registration stage, a luminance of the light source may be set to a maximum luminance. However, it should be noted that, at the biological feature matching stage and the biological feature registration stage, the luminance of the light source may not be necessary to be set to the maximum luminance. Alternatively, the luminance of the light source may be set to a predetermined value, as long as the luminance of the light source at the biological feature matching stage is the same as the biological feature registration stage.

Figure 2:
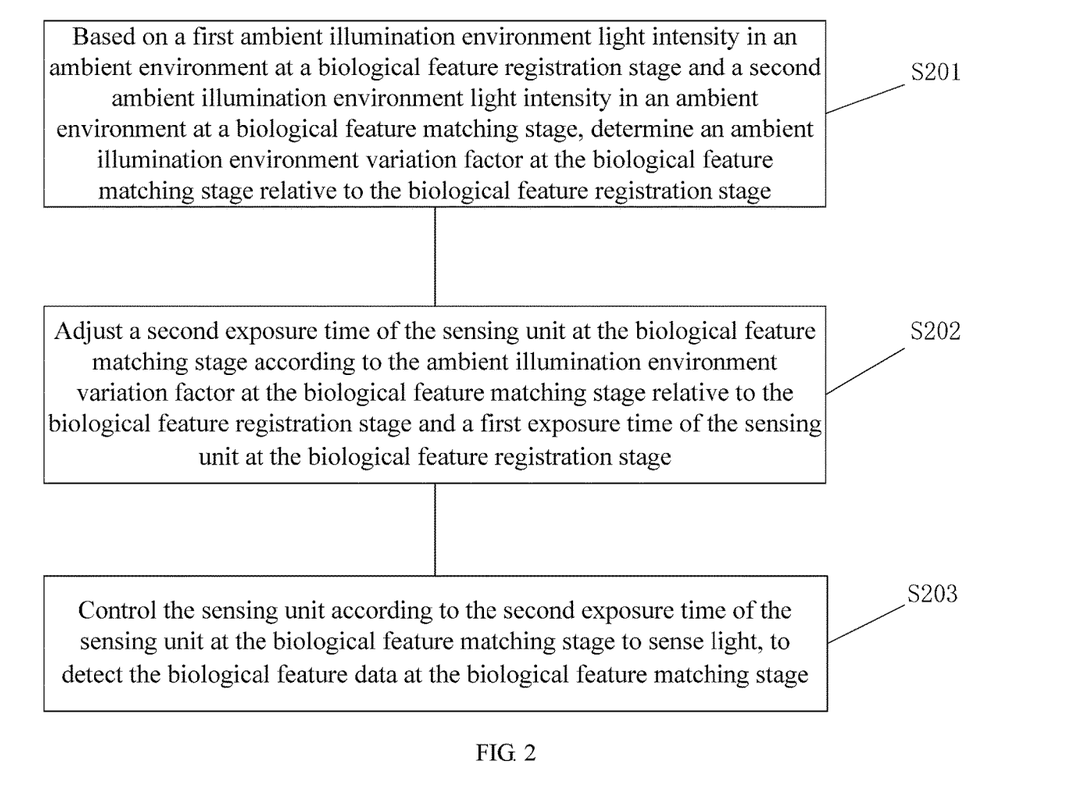
FIG. 2 is a schematic flowchart of a biological feature data detection method according to a second embodiment of the present disclosure.

FIG. 2 is a schematic flowchart of a biological feature data detection method according to a second embodiment of the present disclosure. In this embodiment, ADC gain coefficients of the sensing unit at a biological feature registration stage and a biological feature matching stage are maintained unchanged, but an exposure time of the sensing unit at the biological feature matching stage is adjusted. As specifically illustrated in FIG. 2, the method according to this embodiment includes the following steps:

S201: Based on a first ambient illumination environment light intensity in an ambient environment at a biological feature registration stage and a second ambient illumination environment light intensity in an ambient environment at a biological feature matching stage, an ambient illumination environment variation factor at the biological feature matching stage relative to the biological feature registration stage is determined.

In this embodiment, specific process of step S201 may be referenced to the embodiment as illustrated in FIG. 1, which is not given herein any further. However, it should be noted that this embodiment differs from the first embodiment in that luminance of light source at the biological feature registration stage and the biological feature matching stage is set to a fixed value, that is, a maximum value. Therefore, it may be unnecessary to acquire the light intensity of the light source at the biological feature registration stage and the biological feature matching stage.

S202: A second exposure time of a sensing unit at the biological feature matching stage is adjusted according to the ambient illumination environment variation factor at the biological feature matching stage relative to the biological feature registration stage and a first exposure time of the sensing unit at the biological feature registration stage.

In this embodiment, the second exposure time is as illustrated by formula (2):

$$expo2 = \gamma * expo1 * \frac{n_1}{n_2} \quad (2)$$

In the above formula, expo1 represents a first exposure time, expo2 represents a second exposure time, γ represents a filter coefficient, and n1/n2 represents an ambient illumination environment variation factor.

In this embodiment, as seen from formula (2), the second exposure time expo2 is inversely proportional to the second ambient illumination environment light intensity n2, and the second ambient illumination environment light intensity corresponds to the biological feature matching stage. The greater the ambient illumination environment light intensity at the biological feature matching stage is, the smaller the second exposure time expo2. Moreover, the second exposure time expo2 is proportional to the first exposure time expo1. The greater the first exposure time expo1, the greater the second exposure time expo2.

S203: The sensing unit is controlled to sense light according to the second exposure time of the sensing unit at the biological feature matching stage, to detect the biological feature data at the biological feature matching stage.

Adjustment of the second exposure time and light sensing control of the sensing unit may enable quality of the biological feature data at the biological feature matching stage to be at least approximate to quality of the biological feature data at the biological feature registration stage.

In this embodiment, a light sensing duration of the sensing unit is controlled according to the second exposure time, such that the photosensitive environment at the registration stage is similar to that at the identification stage as much as possible. In this way, the quality of the biological feature data at the biological feature matching stage is at least approximate to the quality of the biological feature data at the biological feature registration stage.

It should be noted that if the exposure time at the biological feature registration stage needs to be adjusted, reference may also be made to the solution disclosed in the embodiment as illustrated in FIG. 2 to adjust the exposure time at the biological feature registration stage.

Figure 3:
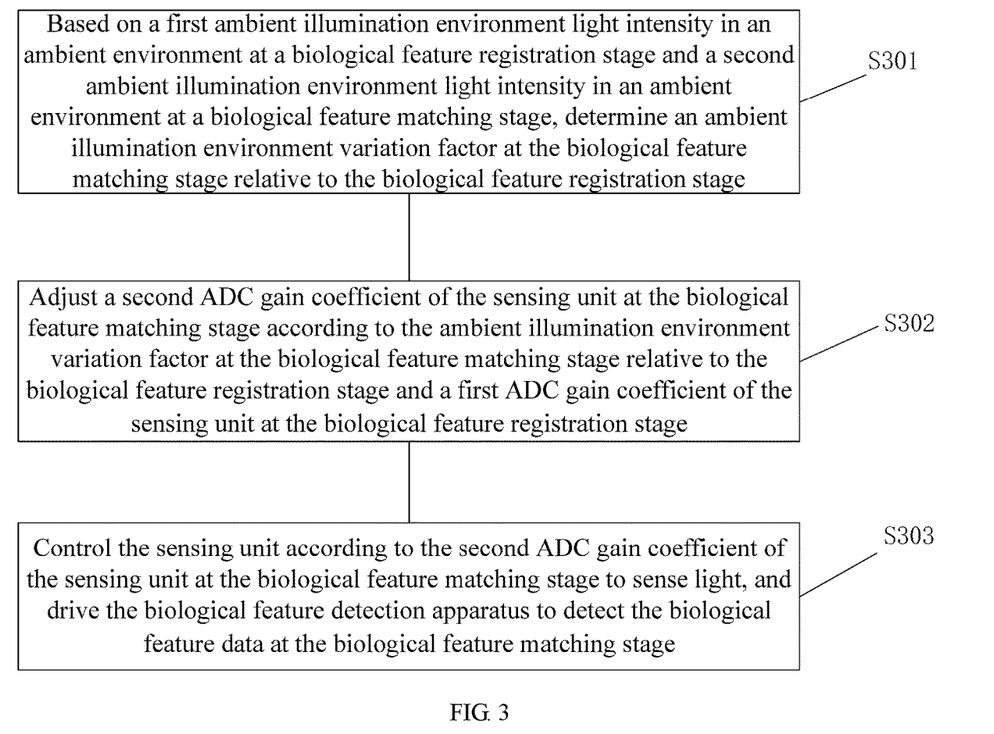
FIG. 3 is a schematic flowchart of a biological feature data detection method according to a third embodiment of the present disclosure.

FIG. 3 is a schematic flowchart of a biological feature data detection method according to a third embodiment of the present disclosure. In this embodiment, exposure times of the sensing unit at a biological feature registration stage and a biological feature matching stage are maintained unchanged, that is, an exposure time at the biological feature registration stage is equal to an exposure time at the biological feature matching stage. Instead, an ADC gain coefficient of the sensing unit at the biological feature matching stage is adjusted. As specifically illustrated in FIG. 3, the method according to this embodiment includes the following steps:

S301: Based on a first ambient illumination environment light intensity in an ambient environment at a biological feature registration stage and a second ambient illumination environment light intensity in an ambient environment at a biological feature matching stage, an ambient illumination environment variation factor at the biological feature matching stage relative to the biological feature registration stage is determined.

In this embodiment, specific process of step S301 may be referenced to the embodiment as illustrated in FIG. 1, which is not given herein any further. However, it should be noted that, similar to the second embodiment, in this embodiment, the luminance of light source at the biological feature registration stage and the biological feature matching stage is set to a fixed value, that is, a maximum value.

S302: A second ADC gain coefficient of a sensing unit at the biological feature matching stage is adjusted according to the ambient illumination environment variation factor at the biological feature matching stage relative to the biological feature registration stage and a first ADC gain coefficient of the sensing unit at the biological feature registration stage.

In this embodiment, the second ADC gain coefficient is as illustrated by formula (3):

$$\text{gain2} = \beta * \text{gain1} * \frac{n_1}{n_2} \quad (3)$$

In the above formula, gain1 represents a first ADC gain coefficient, gain2 represents a second ADC gain coefficient, β represents a filter coefficient, and n1/n2 represents an ambient illumination environment variation factor.

In this embodiment, as seen from formula (3), the second ADC gain coefficient gain2 is inversely proportional to the second ambient illumination environment light intensity n2, and the second ambient illumination environment light intensity corresponds to the biological feature matching stage. The greater the ambient illumination environment light intensity at the biological feature matching stage, the smaller the second ADC gain coefficient gain2. Moreover, the second ADC gain coefficient gain2 is proportional to the first ADC gain coefficient gain1. The greater the first ADC gain coefficient gain1, the greater the second ADC gain coefficient gain2.

S303: The sensing unit of the biological feature identification apparatus is controlled to sense light according to the second ADC gain coefficient of the sensing unit at the biological feature matching stage, to detect the biological feature data at the biological feature matching stage.

Adjustment of the second ADC gain coefficient and light sensing control of the sensing unit may enable quality of the biological feature data at the biological feature matching stage to be at least approximate to quality of the biological feature data at the biological feature registration stage.

It should be noted that if the exposure time at the biological feature registration stage needs to be adjusted, reference may also be made to the solution disclosed in the embodiment as illustrated in FIG. 3 to adjust the exposure time at the biological feature registration stage.

Figure 4:
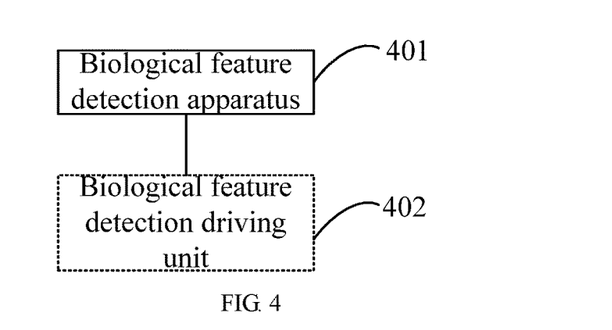
FIG. 4 is a schematic structural diagram of a biological feature identification apparatus according to a fourth embodiment of the present disclosure.

FIG. 4 is a schematic structural diagram of a biological feature identification apparatus according to a fourth embodiment of the present disclosure. As illustrated in FIG. 4, the biological feature identification apparatus includes: a biological feature detection apparatus 401 and a biological feature detection driving unit 402.

The biological feature detection driving unit 402 is configured to: determine, based on a first illumination environment parameter in an ambient environment at a biological feature registration stage and a second illumination environment parameter in an ambient environment at a biological feature matching stage, an ambient illumination environment variation factor of the biological feature detection apparatus 401 at the biological feature matching stage relative to the biological feature registration stage; and adjust a quality influence factor of biological feature data at the biological feature matching stage according to the ambient illumination environment variation factor at the biological feature matching stage relative to the biological feature registration stage, and drive the biological feature detection apparatus to detect the biological feature data at the biological feature matching stage.

Adjustment of the quality influence factor of the biological feature data may enable quality of the biological feature data detected by the biological feature detection apparatus 401 at the biological feature matching stage to be at least approximate to quality of the biological feature data detected by the biological feature detection apparatus 401 at the biological feature registration stage.

Optionally, in an embodiment of the present disclosure, the biological feature detection driving unit 402 is configured to determine the ambient illumination environment variation factor at the biological feature matching stage relative to the biological feature registration stage according to a first ambient illumination environment light intensity in the ambient environment at the biological feature registration stage and a second ambient illumination environment light intensity in the ambient environment at the biological feature matching stage, the first ambient illumination environment light intensity being used as the first illumination environment parameter, and the second ambient illumination environment light intensity being used as the second illumination environment parameter.

Optionally, in an embodiment of the present disclosure, the biological feature detection driving unit 402 is configured to adjust a light intensity of a light source of the biological feature detection apparatus at the biological feature matching stage according to the ambient illumination environment variation factor at the biological feature matching stage relative to the biological feature registration stage.

Exemplarily, in an embodiment of the present disclosure, the biological feature detection driving unit 402 is further configured to determine a second light intensity of the light source at the biological feature matching stage according to the ambient illumination environment variation factor at the biological feature matching stage relative to the biological feature registration stage and a first light intensity of the light source at the biological feature registration stage. Specifically, the biological feature detection driving unit 402 is configured to control a driving signal of the light source to adjust the second light intensity of the light source at the biological feature registration stage.

Alternatively, in an embodiment of the present disclosure, the biological feature detection driving unit 402 is configured to adjust an operation parameter of the sensing unit at the biological feature matching stage according to the ambient illumination environment variation factor at the biological feature matching stage relative to the biological feature registration stage and an operation parameter of the sensing unit at the biological feature registration stage.

Exemplarily, in an embodiment of the present disclosure, the biological feature detection driving unit 402 is configured to adjust a second exposure time of the sensing unit at the biological feature matching stage according to the ambient illumination environment variation factor at the biological feature matching stage relative to the biological feature registration stage and a first exposure time of the sensing unit at the biological feature registration stage.

Further exemplarily, in an embodiment of the present disclosure, the biological feature detection driving unit 402 is configured to adjust a second ADC gain coefficient of the sensing unit at the biological feature matching stage according to the ambient illumination environment variation factor at the biological feature matching stage relative to the biological feature registration stage and a first ADC gain coefficient of the sensing unit at the biological feature registration stage.

Detailed description in this embodiment may be referenced to the disclosure in FIG. 1, FIG. 2 or FIG. 3, which is not given herein any further.

Figure 5:
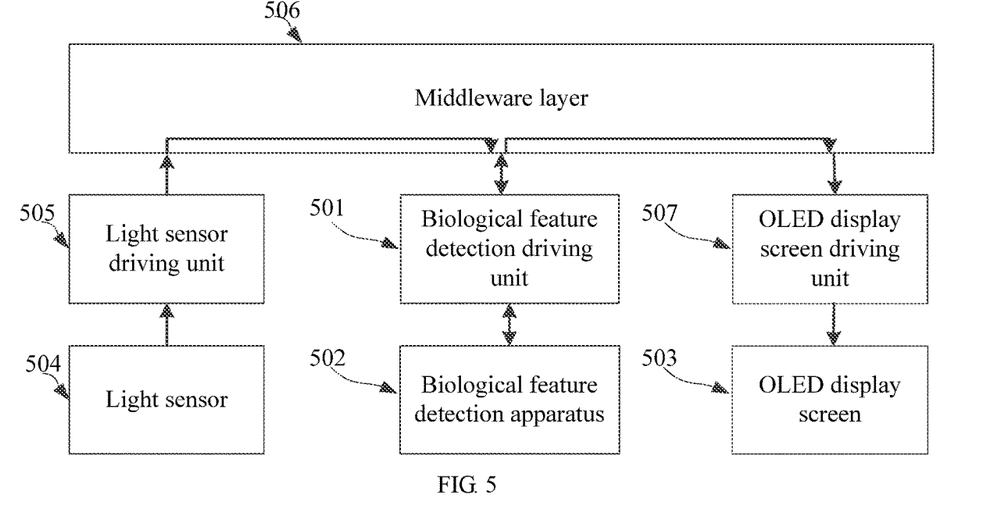
FIG. 5 is a schematic application diagram illustrating operation of a biological feature identification apparatus according to a fifth embodiment of the present disclosure.

FIG. 5 is a schematic application diagram of a biological feature identification apparatus according to a fifth embodiment of the present disclosure. In this embodiment, description is given using an example that the biological feature identification apparatus uses organic light-emitting diodes (OLEDs) in an OLED display screen as a light source.

As illustrated in FIG. 5, at a biological feature registration stage, a biological feature detection driving unit 501 drives a biological feature detection apparatus 502, while pre-acquiring a fingerprint feature image, to acquire a first light intensity s1 of an OLED display screen 503 and a first ambient illumination environment light intensity n1; the first ambient illumination environment light intensity n1 is sensed by a light sensor 504 and transmitted by the light sensor 504 to the light sensor driving unit 505.

At a biological feature matching stage, light in an ambient environment may have changed, and the light sensor may acquire a second ambient illumination environment light intensity n2 in the current ambient environment; the light sensor driving unit 505 may acquire the second ambient illumination environment light intensity n2, and report the second ambient illumination environment light intensity n2 to a middleware layer. Likewise, the biological feature detection driving unit 501 acquires the second ambient illumination environment light intensity n2 by using the middleware layer 506; upon acquiring the second ambient illumination environment light intensity n2, the biological feature detection driving unit 501 determines a second light intensity s2 according to a first light intensity s1, the first ambient illumination environment light intensity n1 and the second ambient illumination environment light intensity n2; and the OLED display screen driving unit 507 drives the OLED display screen according to the second light intensity, and drives the biological feature detection apparatus to detect the biological feature data at the biological feature matching stage. Detailed description may be referenced to the disclosure in the first embodiment.

Figure 6:
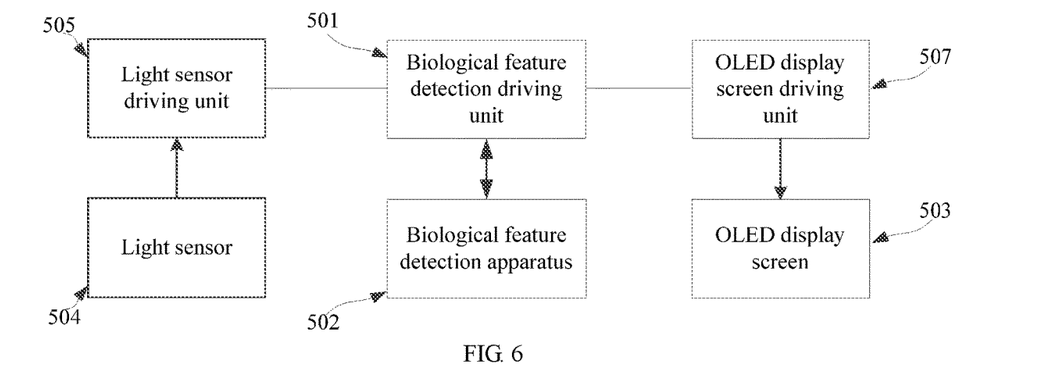
FIG. 6 is a schematic application diagram illustrating operation of a biological feature identification apparatus according to a sixth embodiment of the present disclosure.

FIG. 6 is a schematic application diagram illustrating operation of a biological feature identification apparatus according to a sixth embodiment of the present disclosure. As illustrated in FIG. 6, similar to the fifth embodiment, in this embodiment, description is given using an example that the biological feature identification apparatus uses OLEDs in the OLED display screen 503 as a light source.

At a biological feature registration stage, while the biological feature detection driving unit 501 drives the biological feature detection apparatus 502 to pre-acquire a fingerprint feature image, and the biological feature detection driving unit 501 is configured to instruct an OLED display screen driving unit 507 to set the light intensity to a maximum luminance; and the first ambient illumination environment light intensity n1 is read by using the light sensor driving unit 505.

At a biological feature matching stage, the light sensor 504 acquires the second ambient illumination environment light intensity n2 in the current ambient environment, and correspondingly the light sensor driving unit 505 reads the second ambient illumination environment light intensity n2. Likewise, the biological feature detection driving unit 501 acquires the second ambient illumination environment light intensity n2 by using the light sensor driving unit 505; the biological feature detection driving unit 501 determines operation parameters at the biological feature matching stage according to the first ambient illumination environment light intensity n1, the second ambient illumination environment light intensity n2 and the operation parameters at the biological feature registration stage, and drives the biological feature detection apparatus to detect the biological feature data at the biological feature matching stage. The detailed description may be referenced to the disclosure in the second embodiment and the third embodiment.

Figure 7:
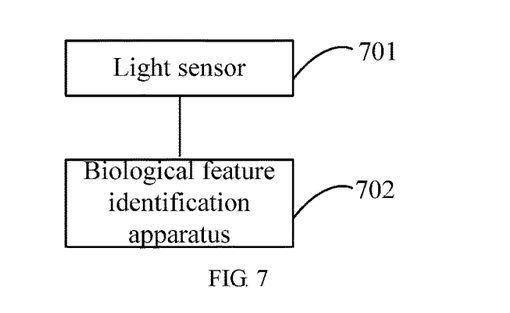
FIG. 7 is a schematic structural diagram of an electronic terminal according to a seventh embodiment of the present disclosure.

FIG. 7 is a schematic structural diagram of an electronic terminal according to a seventh embodiment of the present disclosure. As illustrated in FIG. 7, the electronic terminal includes a light sensor 701, and a biological feature identification apparatus 702 as described in any of the above embodiments. The light sensor 701 is configured to determine a first illumination environment parameter of the biological feature identification apparatus 702 in an ambient environment at a biological feature registration stage and a second illumination environment parameter of the biological feature identification apparatus 702 in an ambient environment at a biological feature matching stage respectively. Details of the light sensor 701 may be referenced to related description of FIG. 5 or FIG. 6.

The electronic device in this embodiment is practiced in various forms, including, but not limited to:

(1) a mobile communication device: which has the mobile communication function and is intended to provide mainly voice and data communications; such terminals include: a smart phone (for example, an iPhone), a multimedia mobile phone, a functional mobile phone, a low-end mobile phone and the like;

(2) an ultra mobile personal computer device: which pertains to the category of personal computers and has the computing and processing functions, and additionally has the mobile Internet access feature; such terminals include: a PDA, an MID, an UMPC device and the like, for example, an iPad;

(3) a portable entertainment device: which displays and plays multimedia content; such devices include: an audio or video player (for example, an iPod), a palm game machine, an electronic book, and a smart toy, and a portable vehicle-mounted navigation device;

(4) a server: which provides services for computers, and includes a processor, a hard disk, a memory, a system bus and the like; the server is similar to the general computer in terms of architecture; however, since more reliable services need to be provided, higher requirements are imposed on the processing capability, stability, reliability, security, extensibility, manageability and the like of the device; and (5) other electronic device having data interaction function.

Figure 8:
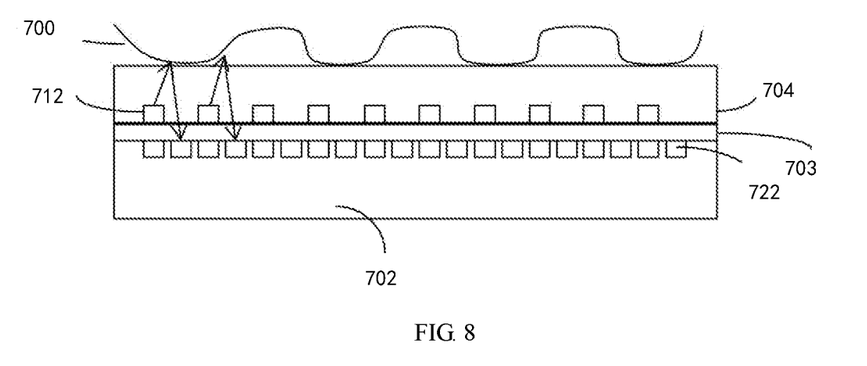
FIG. 8 is a schematic application diagram of a biological feature identification apparatus according to an eighth embodiment of the present disclosure.

FIG. 8 is a schematic application diagram of a biological feature identification apparatus according to an eighth embodiment of the present disclosure. As illustrated in FIG. 8, in this embodiment, description is given using an example that the biological feature identification apparatus 702 uses organic light-emitting diodes (OLEDs) in an OLED display screen 704 as a light source. As illustrated in FIG. 8, a sensing unit 722 in the biological feature identification apparatus 702 is arranged below an optical filter 703. OLEDs are arranged on the optical filter 703 as the light source 712. Light emitted by the OLEDs is reflected by a finger 700, passes through the optical filter 703 and processed by the optical filter 703, and is finally sensed by the sensing unit 722, thereby generating a fingerprint feature image.

Technical description of operation of the biological feature identification apparatus in this embodiment may be referenced to the disclosure of the embodiment as illustrated in FIG. 4, which is not given herein any further.

The above described apparatus embodiments are merely for illustration purpose only. The modules which are described as separate components may be physically separated or may be not physically separated, and the components which are illustrated as modules may be or may not be physical modules, that is, the components may be located in the same position or may be distributed into a plurality of network modules. A part or all of the modules may be selected according to the actual needs to achieve the objectives of the technical solutions of the embodiments. Persons of ordinary skill in the art may understand and implement the present application without paying any creative effort.

According to the above embodiments of the present application, a person skilled in the art may clearly understand that the embodiments of the present application may be implemented by means of hardware or by means of software plus a necessary general hardware platform. Based on such understanding, portions of the technical solutions of the present application that essentially contribute to the related art may be embodied in the form of a software product, the computer software product may be stored in a computer readable storage medium. The computer-readable storage medium includes any mechanism for storing or transferring information in a computer readable form. For example, the computer-readable medium includes a read-only memory (ROM), a random access memory (RAM), a disk storage medium, an optical storage medium, a flash storage medium, electricity, light, sound and other forms of propagation signals (for example, a carrier, an infrared signal, a digital signal and the like), and the like. The computer software product includes several instructions for instructing a computer device (which may be a personal computer, a server, or a network device) to perform all the embodiments or some parts of the embodiments.

The present disclosure is described based on the flowcharts and/or block diagrams of the method, apparatus (device), and computer program product. It should be understood that each process and/or block in the flowcharts and/or block diagrams, and any combination of the processes and/or blocks in the flowcharts and/or block diagrams may be implemented using computer program instructions. These computer program instructions may be issued to a computer, a dedicated computer, an embedded processor, or processors of other programmable data processing device to generate a machine, which enables the computer or the processors of other programmable data processing devices to execute the instructions to implement an apparatus for implementing specific functions in at least one process in the flowcharts and/or at least one block in the block diagrams.

These computer program instructions may also be stored a non-transitory computer-readable memory capable of causing a computer or other programmable data processing devices to work in a specific mode, such that the instructions stored on the non-transitory computer-readable memory implement a product comprising an instruction apparatus, where the instruction apparatus implements specific functions in at least one process in the flowcharts and/or at least one block in the block diagrams.

These computer program instructions may also be stored on a computer or other programmable data processing devices, such that the computer or the other programmable data processing devices execute a series of operations or steps to implement processing of the computer. In this way, the instructions, when executed on the computer or the other programmable data processing devices, implement the specific functions in at least one process in the flowcharts and/or at least one block in the block diagrams.

Although the preferred embodiments of the present application are described above, once knowing the basic creative concept, a person skilled in the art can make other modifications and variations to these embodiments. Therefore, the appended claims are intended to be construed as covering the preferred embodiments and all the modifications and variations falling within the scope of the present application. Obviously, a person skilled in the art can make various modifications and variations to the present application without departing from the spirit and scope of the present application. In this way, the present application is intended to cover the modifications and variations if they fall within the scope of the appended claims of the present application and equivalent technologies thereof.

What is claimed is:

1. A biological feature data detection method for a biological feature detection apparatus, the biological feature data detection method comprising:
    determining, based on a first illumination environment parameter in an ambient environment at a biological feature registration stage and a second illumination environment parameter in an ambient environment at a biological feature matching stage, an ambient illumination environment variation factor at the biological feature matching stage relative to the biological feature registration stage; and
    adjusting a quality influence factor of the biological feature data at the biological feature matching stage according to the ambient illumination environment variation factor at the biological feature matching stage relative to the biological feature registration stage so that at least one of image clarity and noise of a biological feature image obtained from the biological feature data at the biological feature matching stage approximates at least one of image clarity and noise of a biological feature image obtained from the biological feature data at the biological feature registration stage, and detecting the biological feature data at the biological feature matching stage,
    wherein the biological feature detection apparatus comprises a sensing unit, and the adjusting a quality influence factor of the biological feature data at the biological feature matching stage according to the ambient illumination environment variation factor at the biological feature matching stage relative to the biological feature registration stage comprises:
    adjusting an operation parameter of the sensing unit at the biological feature matching stage according to the ambient illumination environment variation factor at the biological feature matching stage relative to the biological feature registration stage and the operation parameter of the sensing unit at the biological feature registration stage, wherein the operation parameter comprises an exposure time.

2. The method according to claim 1, wherein an ADC gain coefficient is set to a constant value, and correspondingly, the adjusting an operation parameter of the sensing unit at the biological feature matching stage according to the ambient illumination environment variation factor at the biological feature matching stage relative to the biological feature registration stage and the operation parameter of the sensing unit at the biological feature registration stage comprises:
    adjusting a second exposure time of the sensing unit at the biological feature matching stage according to the ambient illumination environment variation factor at the biological feature matching stage relative to the biological feature registration stage and a first exposure time of the sensing unit at the biological feature registration stage.

3. A biological feature identification apparatus, comprising:
- a biological feature detection apparatus and a biological feature detection driving unit;
- wherein the biological feature detection driving unit is configured to:
- determine, based on a first illumination environment parameter in an ambient environment at a biological feature registration stage and a second illumination environment parameter in an ambient environment at a biological feature matching stage, an ambient illumination environment variation factor of the biological feature detection apparatus at the biological feature matching stage relative to the biological feature registration stage; and
- adjust a quality influence factor of biological feature data at the biological feature matching stage according to the ambient illumination environment variation factor at the biological feature matching stage relative to the biological feature registration stage so that at least one of image clarity and noise of a biological feature image obtained from the biological feature data at the biological feature matching stage approximates at least one of image clarity and noise of a biological feature image obtained from the biological feature data at the biological feature registration stage, and drive the biological feature detection apparatus to detect the biological feature data at the biological feature matching stage,
- wherein the biological feature detection apparatus comprises a sensing unit, and the biological feature detection driving unit is configured to adjust an operation parameter of the sensing unit at the biological feature matching stage according to the ambient illumination environment variation factor at the biological feature matching stage relative to the biological feature registration stage and the operation parameter of the sensing unit at the biological feature registration stage, wherein the operation parameter comprises an exposure time.

4. The biological feature identification apparatus according to claim 3, wherein an ADC gain coefficient is set to a constant value, and correspondingly biological feature detection driving unit is configured to adjust a second exposure time of the sensing unit at the biological feature matching stage according to the ambient illumination environment variation factor at the biological feature matching stage relative to the biological feature registration stage and a first exposure time of the sensing unit at the biological feature registration stage.

5. An electronic terminal, comprising:
- a light sensor and a biological feature identification apparatus;
- wherein the light sensor is configured to determine a first illumination environment parameter in an ambient environment at a biological feature registration stage and a second illumination environment parameter in an ambient environment at a biological feature matching stage respectively;
- the biological feature identification apparatus comprises a biological feature detection apparatus and a biological feature detection driving unit;
- wherein the biological feature detection driving unit is configured to:
- determine, based on a first illumination environment parameter in an ambient environment at a biological feature registration stage and a second illumination environment parameter in an ambient environment at a biological feature matching stage, an ambient illumination environment variation factor of the biological feature detection apparatus at the biological feature matching stage relative to the biological feature registration stage; and
- adjust a quality influence factor of biological feature data at the biological feature matching stage according to the ambient illumination environment variation factor at the biological feature matching stage relative to the biological feature registration stage so that at least one of image clarity and noise of a biological feature image obtained from the biological feature data at the biological feature matching stage approximates at least one of image clarity and noise of a biological feature image obtained from the biological feature data at the biological feature registration stage, and drive the biological feature detection apparatus to detect the biological feature data at the biological feature matching stage,
- wherein the biological feature detection apparatus further comprises a sensing unit, and the biological feature detection driving unit is configured to adjust an operation parameter of the sensing unit at the biological feature matching stage according to the ambient illumination environment variation factor at the biological feature matching stage relative to the biological feature registration stage and the operation parameter of the sensing unit at the biological feature registration stage, wherein the operation parameter comprises an exposure time.

* * * * *